United States Patent [19]

Zinopoulos et al.

[11] Patent Number: 4,850,965
[45] Date of Patent: Jul. 25, 1989

[54] HYDRAULIC APPARATUS FOR BODILY HYGIENE

[76] Inventors: Jean Zinopoulos; Andre Zinopoulos, both of BP 25, 13170 La Gavotte, France

[21] Appl. No.: 948,194

[22] Filed: Dec. 31, 1986

[51] Int. Cl.[4] ............................................. A61M 31/00
[52] U.S. Cl. ...................................... 604/73; 604/275; 604/131; 239/397; 239/447
[58] Field of Search ............... 604/131, 257, 275, 278, 604/279, 73; 239/391, 392, 397, 447, 557, 562, 568; 137/625.11, 873, 862; 401/136

[56] References Cited

U.S. PATENT DOCUMENTS 151,823  6/1874  Baldwin ............................. 239/392

FOREIGN PATENT DOCUMENTS 1060141 11/1953  France ................................. 401/136
499311  4/1970  Switzerland .
10783  5/1911  United Kingdom ................ 401/136

Primary Examiner—Stephen C. Pellegrino
Attorney, Agent, or Firm—William A. Drucker

[57] ABSTRACT

Hydraulic apparatus for bodily hygiene comprising a body (1) of which a portion is arranged to constitute a handle (1a) provided with a threading (6) permitting its coupling to a flexible pipe, this body being provided internally with at least two distribution conduits (8,9) and a inlet conduit (7) capable of being placed in communication with one or the other of the distribution conduits, according to the position of a two-position selector (1a-1b-2), and characterized in that one of the distribution conduits (8) opens into a wide cavity (10) constituting the head of the apparatus and bounded by a spray head (11), while the second of the distribution conduits (9) communicates with a coupling mouth piece (12) likewise arranged in the head (1b), and in that the apparatus also comprises a removable attachment (20,23,25,35,41) provided with a fixing ferrule (17) intended to be coupled to the mouth piece, for example by insertion into the latter.

8 Claims, 6 Drawing Sheets

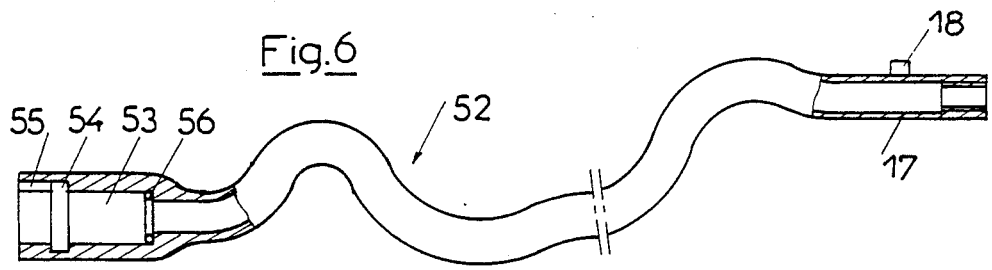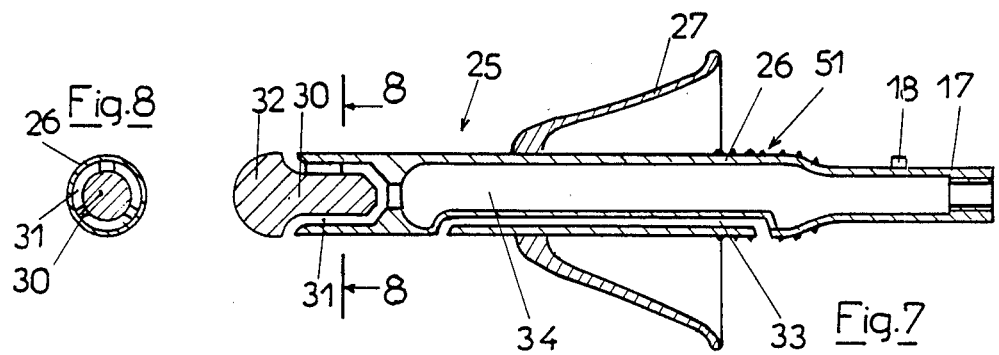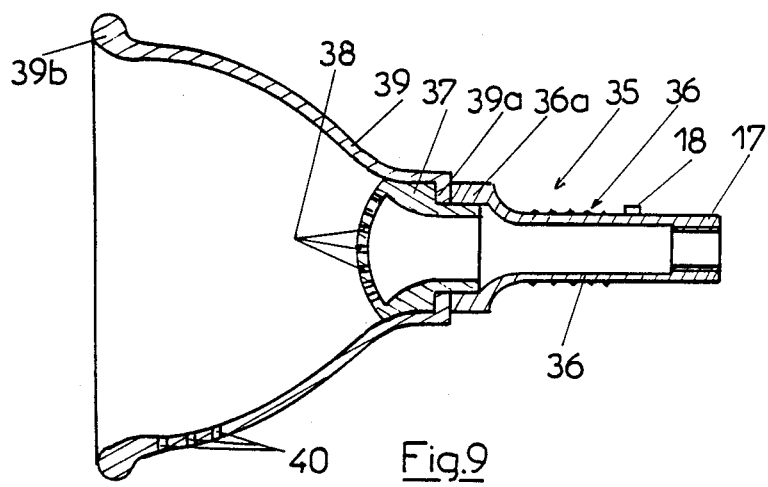

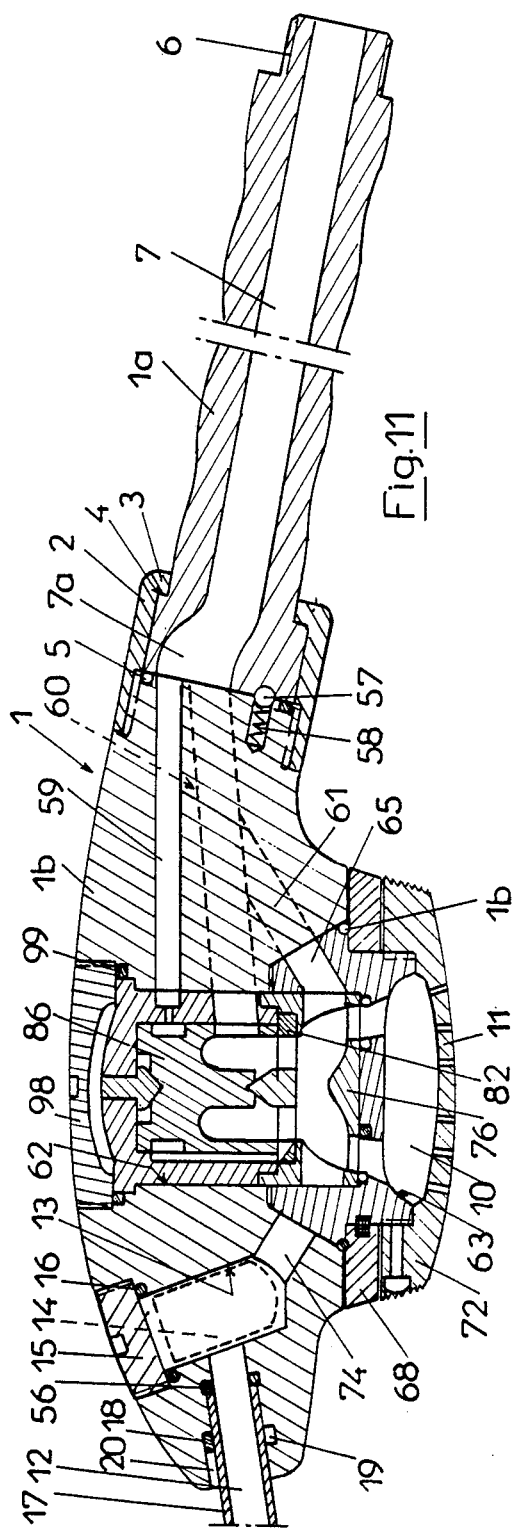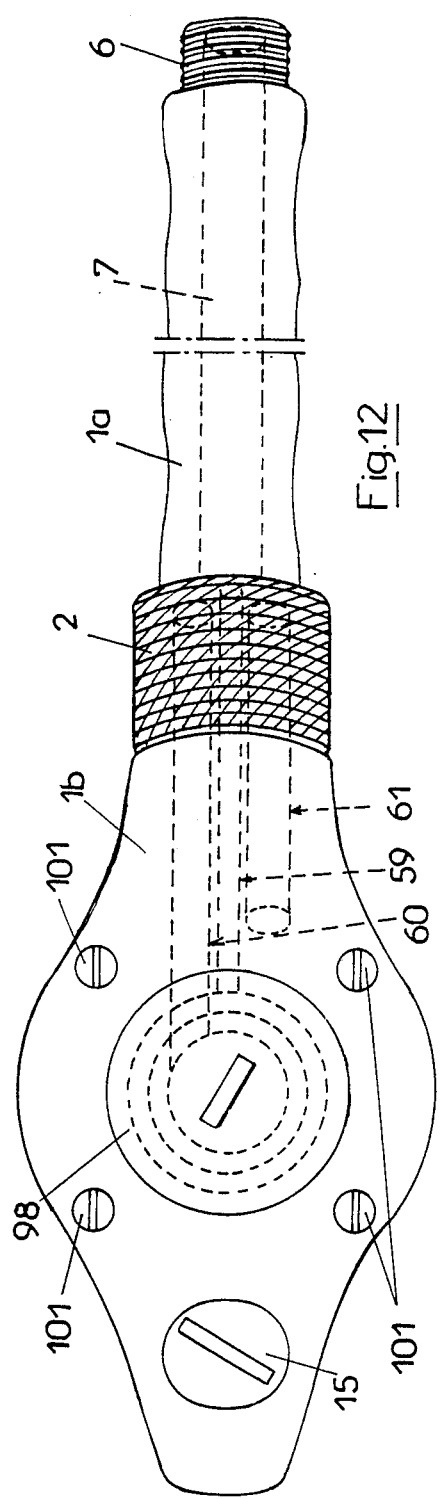

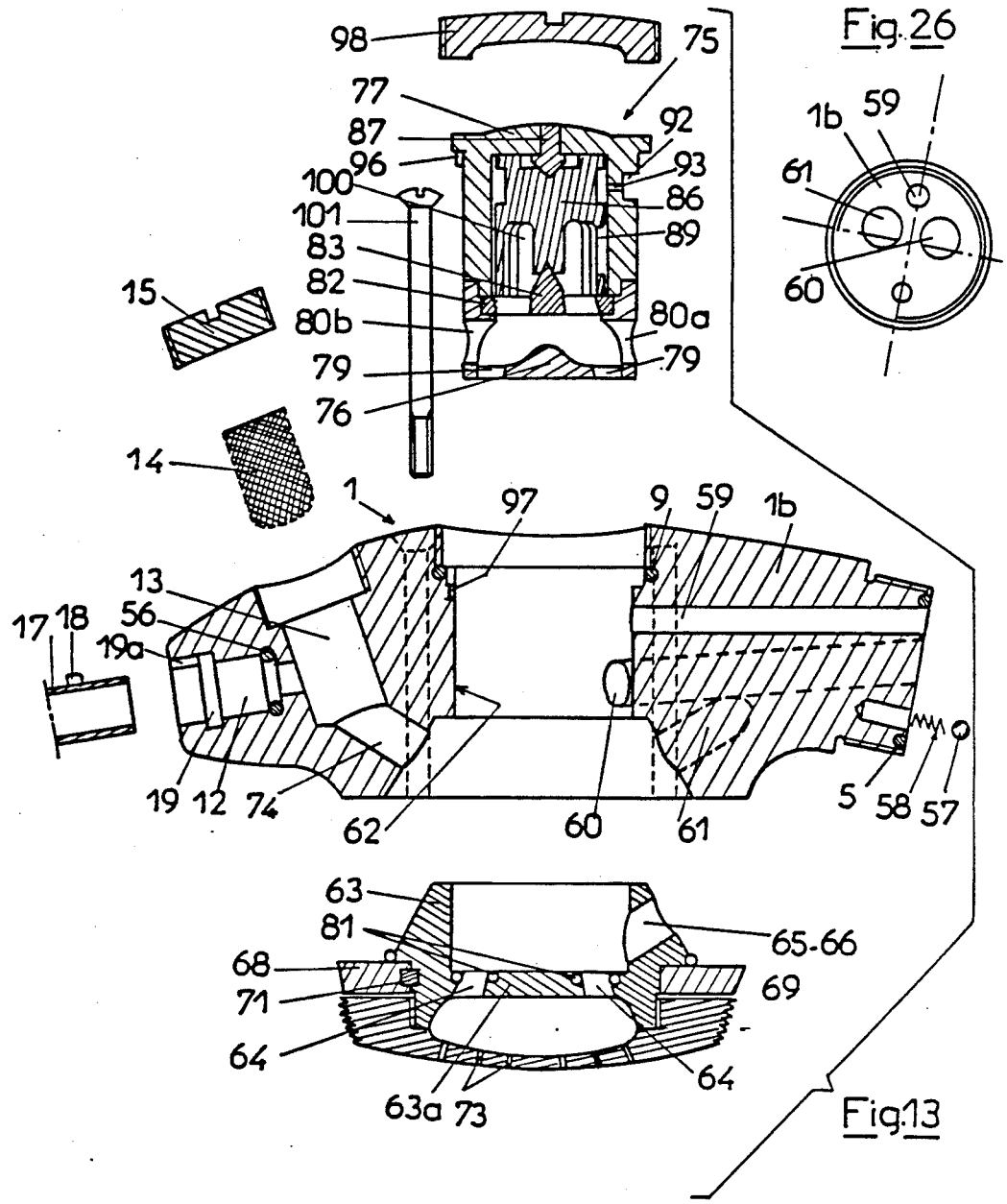

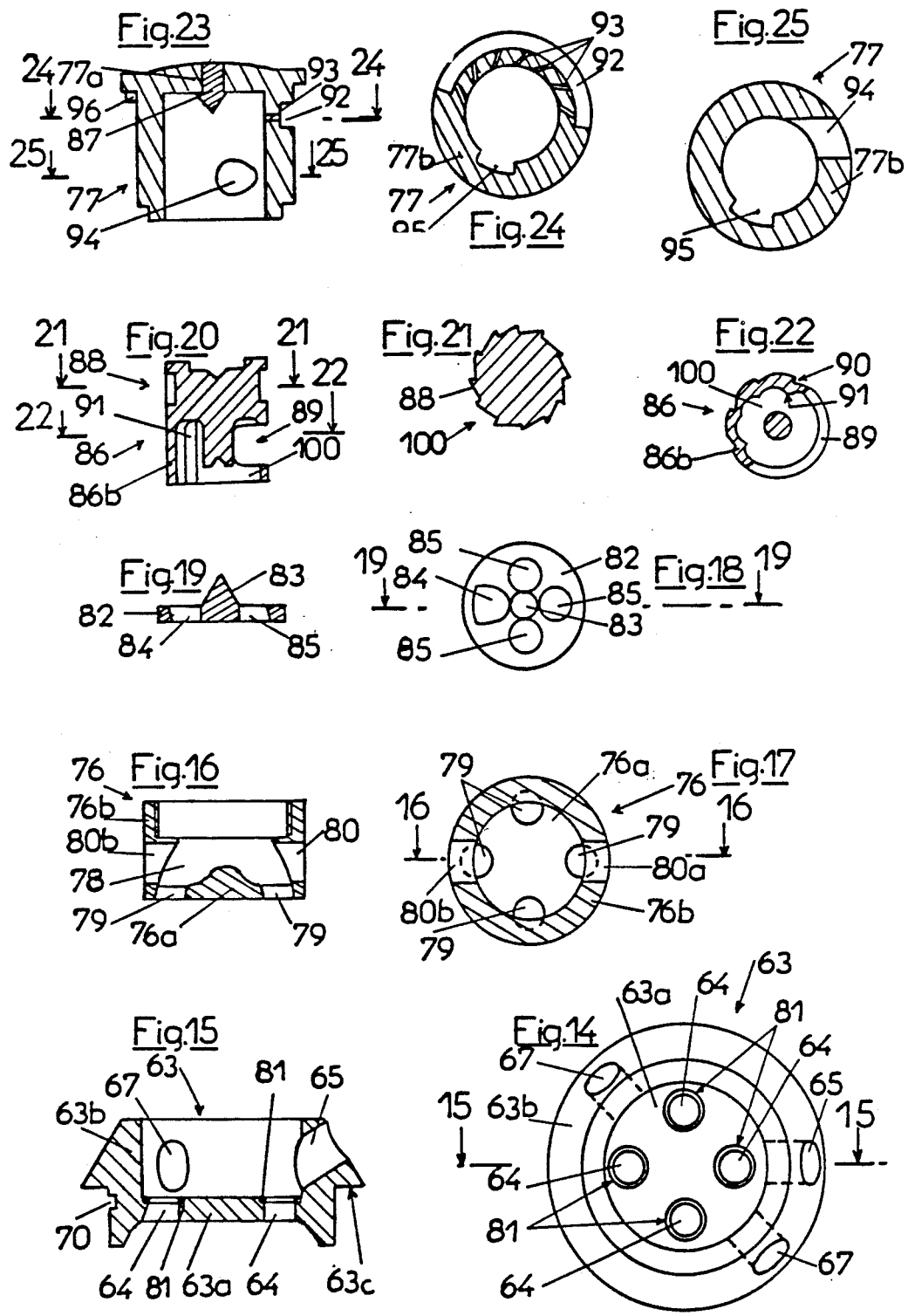

4,850,965

HYDRAULIC APPARATUS FOR BODILY HYGIENE

BACKGROUND OF THE INVENTION

The present invention relates to a hydraulic apparatus for bodily hygiene permitting particularly the washing of all of the parts of the body, including the various anatomical cavities, as well as massage by means of jets of water.

PRIOR ART

There is already known (CH-A-499311) an apparatus for the care of the mouth and teeth comprising a tap with three passages angularly spaced at 90 degrees and comprising three couplings of which one is for the coupling of a water inlet, a second is for the assembly of a delivery ferrule, and a third is for the coupling of a flexible pipe, provided if need be with a buccal spray, or an atomiser, or a special tooth brush, this three-way tap being housed in a casing serving to be fixed on a wall and provided with a projecting operating button.

An apparatus of this kind has several inconveniences and insufficiencies such as:

its fixed mounting which largely limits the possibilities of bodily washing and which brings the necessity of installing a flexible distribution pipe for the connecting of an instrument for buccal lavage;

the straight positioning of the feed conduit and of the two distribution conduits which in practice prevents any possibility of transformation of this fixed apparatus into a mobile apparatus;

the impossibility of incorporating, into the washing water, antiseptic, therapeutic medicinal or other substances;

the absence of the possibility of modification of the characteristics of the jets of water produced.

The inconveniences and insufficiencies of this kind of apparatus result in that bodily hygiene is always currently assured by the use of specialised different water outlets distributed in various sites of bathrooms (washstand, shower, bath, bidet) and by the addition of specific complementary devices such as hydropulsers, washing heads, etc., which have features often badly adapted to their function (reduced volume of water, output too small, pressure sometimes too high, reduced active surface of the jet or jets) and as a consequence, only a relative usefulness, or a harmful action.

OBJECT OF THE INVENTION

The present invention has particularly for its object to remedy the disadvantages arising from the situation mentioned above, as well as the inconveniences and insufficiencies of the apparatus described in the document No. CH-A-499311.

SUMMARY OF THE INVENTION

The hydraulic apparatus according to the invention is in the first place notable from the fact that it comprises a body of which a portion is arranged to constitute a handle provided with a threading permitting its coupling to a flexible inlet pipe, this body being provided internally with two distribution conduits and an inlet conduit capable of being placed in communication with one or the other of the said distribution conduits, according to the position of a two-position selector, one of the said distribution conduits opening into a wide cavity formed in the body and bounded by a perforated wall constituting a spray head, whilst the second of the said distribution conduits communicates with a coupling mouth piece likewise formed in the said body, the said apparatus further comprising a removable attachment provided with a fixing ferrule serving to be coupled to the said mouth piece, for example by insertion into this latter.

The apparatus thus constructed has for its advantage that it is simple, of little encumbrance, of easy handling and also permits the spraying of the body by reason of its spray head, as well as washing or rinsing of the teeth and the hydraulic massage of the gums by using an appropriate attachment, or again, by means of other appropriate attachments, the washing or irrigation vaginally or rectally.

According to another advantageous arrangement of the invention, a cavity provided with a fluid tight closure means is formed in the body of the apparatus, this cavity being disposed upstream of the coupling mouth piece and communicating both with the said mouth piece and with the distribution conduit placed in relation thereto; a strainer being preferably installed in the said cavity.

By reason of this arrangement, it is possible to place salts or other soluble substances in the cavity, these salts being dissolved during the passage of the water through the said cavity, in such a manner that there is obtained, at the outlet of the attachments, according to needs, jets of an antiseptic, medicated or other solution, according to the nature of the said salts.

According to another arrangement which is characteristic of the invention, a pulsator device is disposed on the distribution conduit terminating at the coupling mouth piece and/or on the distribution conduit terminating at the spray head, this pulsator being also able to be placed, in the body, upstream of the two outlet conduits, i.e. at the exterior of the apparatus By reason of these arrangements it is possible to modify the characteristic of the jets of water at the outlet of the attachments, or the spray head, in such a manner as to obtain, according to need, continuous filiform jets, or pulsated, these latter particularly permitting the exertion of an efficacious massage action on the tissues sprayed.

BRIEF DESCRIPTION OF THE DRAWINGS

The objects, features and advantages mentioned above, and still others, will be better apparent from the description which follows and from the accompanying drawings, wherein:

FIG. 6 is a view in perspective, with partial sectioning, of a flexible tubular extension permitting the fitting at a distance of the removable attachments;

FIG. 7 is a view in axial section of a manner of construction of a removable attachment constituted by a small douche intended for internal bodily hygiene (vaginal or rectal);

FIG. 8 is a view in section taken on the line 8—8 of FIG. 7;

FIG. 9 is a view in axial section of a removable attachment constituted by a small hydraulic massage douche;

FIG. 11 is a view in axial section of the manner of construction of the hydraulic apparatus for bodily hygiene in accordance with the invention with the pulsator device disposed in the body FIG. 12 is a plan view of this apparatus;

FIG. 13 is an exploded view in longitudinal section of the head of the said apparatus;

FIG. 14 is a plan view of the selector permitting to direct the water either towards the head of the corporeal douche, or towards the removable attachment mounted on the head of the apparatus;

FIG. 15 is a view in section along the line 15—15 of FIG. 14;

FIG. 16 is a view in axial section of the lower part of the fixed casing containing the movable members of the pulsator;

FIG. 17 is a view in section on the line 17—17 if FIG. 16;

FIG. 18 is a plan view of the lower pivot bearing disc of the pulsator;

FIG. 19 is a view in section along the line 19—19 of FIG. 18;

FIG. 20 is a view in axial section of the turbine of the pulsator;

FIG. 21 is a view in section along the line 21—21 of FIG. 20;

FIG. 22 is a view in section on the line 22—22 of FIG. 20;

FIG. 23 is a view in axial section of the upper part of the casing of the pulsator;

FIG. 24 is a view in section along the line 24—24 of FIG. 23;

FIG. 25 is a view in section along the line 25—25 of FIG. 23;

FIG. 26 is a front elevation of the plane junction end of the rotary head of the apparatus;

DESCRIPTION OF THE PREFERRED EMBODIMENTS

Reference is now made to the said drawings in order to describe advantageous forms of construction, although in no way limitative, of the hydraulic apparatus for bodily hygiene according to the invention.

Figure 1:
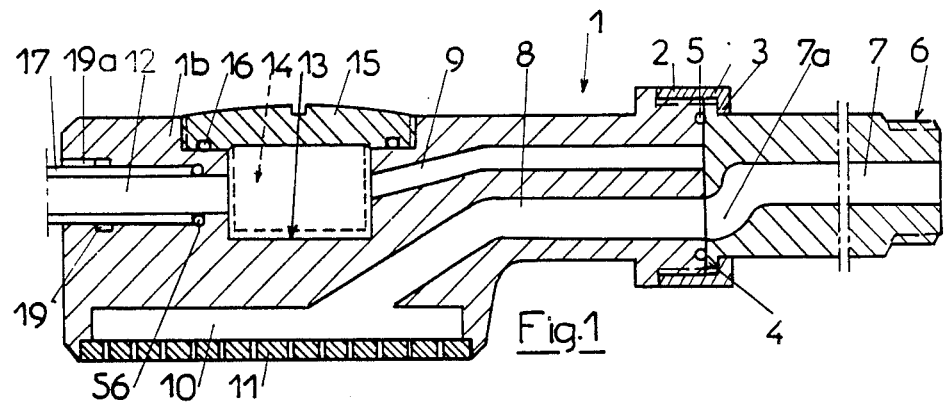
FIG. 1 is a view in axial section of a first simplified manner of construction of the hydraulic apparatus for corporeal hygiene according to the invention, shown in the position permitting the use of the douche.

According to the simplified example of construction illustrated in FIG. 1, this apparatus comprises a body 1 made in two parts 1a, 1b joined one as an extension to the other by means of one of their ends having a plane surface. These parts 1a, 1b are assembled, in fluid tight manner, by means of a coupling device permitting a rotation of one of them about its longitudinal axis. This coupling device comprises, for example, a bored ring 2 screwing onto a thread presented by the rear end of the part 1b, and provided with a circular shoulder 3 bearing against a peripheral shoulder 4 provided on the forward end of the part 1a. The fluid tightness between the surfaces in contact of the parts 1a, 1b is assured by means of an annular joint 5 housed in a recess formed in one of the said surfaces.

The part 1a of the body 1 is arranged to constitute a handle and its rear end is provided with a threading 6 permitting its coupling to a flexible pipe and, of particular interest, to the flexible spray pipe of a mixer tap provided with a suitable coupling.

In the part 1a constituting the handle of the apparatus there is formed a longitudinal inlet conduit 7 the outlet of which 7a is eccentric.

The rotatable part 1b of the body 1 or head of the apparatus comprises two internal distribution conduits 8 and 9 the inlet of which is capable of being placed selectively in association with the eccentric outlet 7a of the inlet conduit 7, by means of rotation of the said part. This arrangement permits the provision of a very simplified selector.

One of the distribution conduits (conduit 8) opens into a broad chamber 10 provided laterally in the part 1b, this chamber being bounded by a perforated wall 11 fixed on the said part and constituting a conventional shower head.

The other distribution conduit (conduit 9) communicates with a coupling mouthpiece which can advantageously be constituted by a cylindrical housing 12 formed longitudinally in the forward part of the body 1.

In an interesting manner, a cavity 13 is formed in the part 1b of the body, upstream of the coupling mouthpiece 12 considered in the direction of flow of the water. The conduit 9 opens into this cavity which communicates with the coupling mouthpiece 12. In the cavity 13 there is installed a strainer 14, and the inlet of the said cavity is provided with a fluid tight closure constituted for example by a stopper 15 provided with an annular sealing joint 16 and fixed by threading.

The apparatus according to the invention further comprises a removable attachment which can have different shapes, according to the use for which it is intended.

There have thus been provided a certain number of types of attachments adapted to different problems of internal or external bodily hygiene.

Each of these removable attachments comprises a ferrule 17 permitting its coupling to the mouthpiece 12. According to the manner of construction illustrated, each attachment has a cylindrical ferrule 17 permitting its engagement and its fixation in the cylindrical mouthpiece 12 of the head 1b.

The fixing ferrule 17 and the mouthpiece 12 are provided with complementary means permitting the locking of the said ferrule in the said mouthpiece. These means are constituted, for example, on the one hand by a radial stud 18 carried by the lateral surface of the ferrule and, on the other hand, by an annular recess 19 formed at the interior of the mouthpiece and into which there opens a longitudinal engagement and disengagement recess 19a. This simple manner of fixing has another advantage of permitting movements of rotation of the attachment installed on the head of the apparatus, with respect to the said head; such movements of limited amplitude can be very useful, for example for washing, rinsing or massaging of the teeth.

Figure 2:
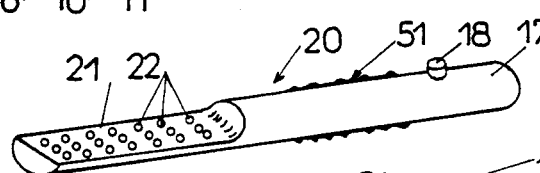
FIGS. 2 and 3 are views in perspective of two advantageous forms of construction of removable attachments intended for bucco-dental hygiene.

FIG. 2 shows an attachment made in the form of a dental spray 20 comprising a flattened forward portion forming a rectangular surface 21 on which there is formed a mesh of circular perforations 22, disposed with or without a break, at the crossing points of straight lines. The inter-axial spacing of the perforations is of the order of 2 to 3 mm.; the number of perforations being 3 to 4 per transverse row. On the other hand, the inter-axial spacing of the longitudinal rows is of the order of 4 to 5 mm.; the number of perforations being 5,6 or 7 per longitudinal row. According to the type and the number of buccal sprays used and of the number of perforations, the diameter of this latter is of the order of 0.5 to 1 mm.

Figure 3:
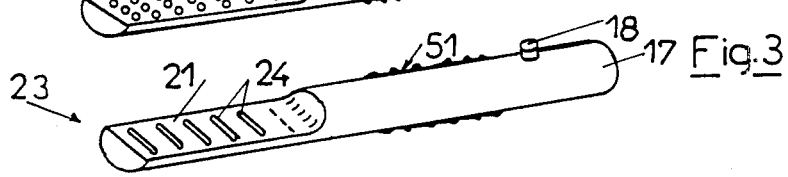

The buccal spray 23 illustrated in FIG. 3 differs from that which has just been described, by the fact that the perforated transverse rows are replaced by spaced transverse openings 24 the ends of which can be widened towards the exterior.

The body of the two attachments is made rectilinear, in the example illustrated in FIGS. 2 and 3. It can be slightly bent in the direction which follows the plane of the perforations or of the openings, in the re-entrant obtuse angle.

The spray 25 illustrated in FIG. 7 is intended for internal bodily irrigation (vaginal or rectal). It comprises an elongated hollow body 26 on which is mounted, with a capability of sliding, a flexible positioning sleeve 27, and of which the rear extremity is constituted by a fixing ferrule 17 provided with its locking stud 18.

Figures 4, 5:
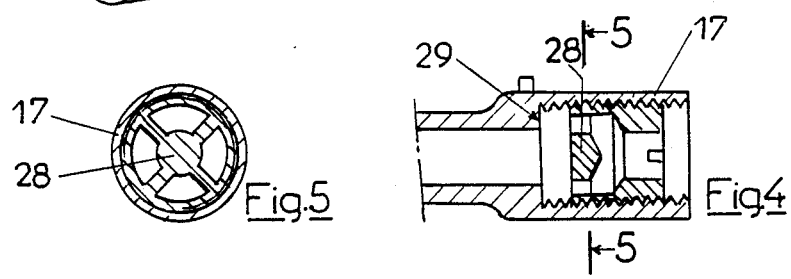
FIG. 4 is a view, in axial section and to a larger scale, of the fixing ferrule of these attachments at the interior of which is mounted an outflow and pressure limiter.
FIG. 5 is a view in section along the line 5—5 of FIG. 4.

At the interior of the ferrule 17 provided with a threading, there is mounted, with a latitude of axial displacement by screwing, an output limiter 28 (FIGS. 4 and 5) permitting the lowering of pressure of the water, by spacing of this latter with respect to a surface 29, for example constituted by the base of the housing of the said output limiter. The adjustment takes place by the user by screwing in this limiter to a greater or lesser extent, this being for a maximum opening of the mixer tap.

A secondary expander for varying output 30 permits to refine this adjustment. The jets of water are produced by the annular nozzle openings 31 of this output variator, the rounded head 32 of which facilitates entry. Channels 33 are formed longitudinally in the body 26, parallel to the principal axis conduit 34, in order to permit a complementary evacuation, the openings 33a,33b of these supplementary channels being formed laterally in the said body.

FIG. 9 shows a spray head for hydraulic massage. This spray head 35 comprises a hollow body 36 of elongated shape the rear end of which is constituted by a fixing ferrule 17 provided with its locking stud 18. At the interior of this ferrule, as at the interior of the fixing ferrule of the various sprays serving to constitute the removable attachment of the apparatus according to the invention, there can be installed an output limiter 28 identical to or comparable with that which equips the spray 25.

The other end 36a of the body 36 is widened and in this widened end there is mounted, for example by screwing, a spray head 37 provided with perforations 38. A flexible sleeve 39 in the shape of a cup is disposed at the forward part of the spray head, this sleeve being for example fixed by its narrowed end 39a between the spray head 37 and the body 36, whilst ensuring fluid tightness between these two members.

The widened end 39b of the sleeve 39 is intended for application against the part of the body to be treated, and the said sleeve comprises, laterally, openings 40 permitting the evacuation of the massage water.

Figure 10:
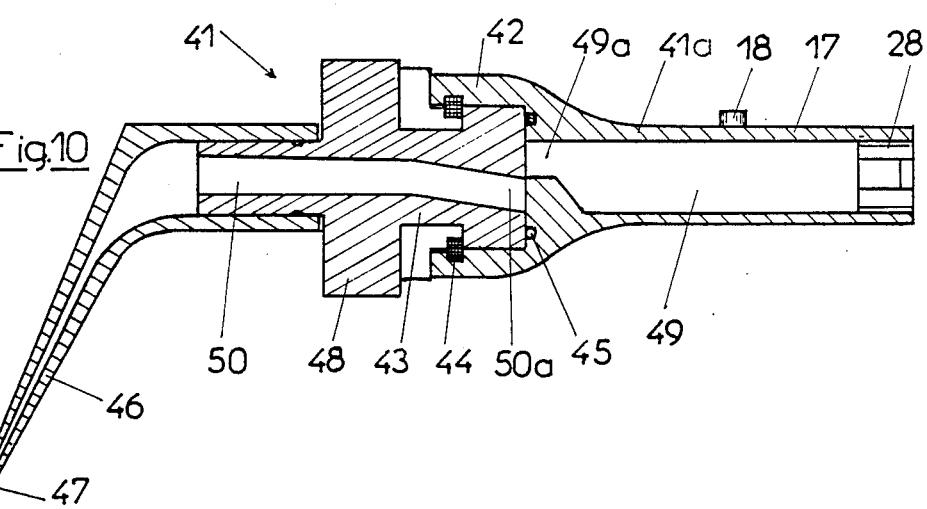
FIG. 10 is a view in axial section of another manner of construction of the removable attachment constituted by an irrigator for the parodontal opening.

FIG. 10 shows an attachment constituted by an irrigator permitting to assure, in association with soluble salts deposited in the cavity 13, an irrigation for example of the parodontal sockets.

This irrigator 41 comprises a hollow body 41a of elongated shape the rear end of which is constituted by a fixing ferrule 17 provided with its locking lug 18 and comprising, advantageously, internally a principal output limiter 28. The other end of the body 41a is widened and in this widened end 42 there is mounted, with a capability of rotation, a secondary output limiter 43 kept in its housing by circular clips 44. An annular joint 45 ensures the fluid tightness between the surfaces in contact of the body 41a and the output limiter 43. On the front end of the output limiter there is mounted an angled or straight ejection ferrule 46 made of semiflexible plastics material with a soft tip 47. A knurled wheel 48, integral with the body of the output limiter 43, facilitates the operation of this latter. Contiguous openings 49a,50a of the conduits 49,50 respectively formed in the body 41 and in the output limiter 43 are eccentric in such a manner that the complementary adjustment of output can be obtained by making the said openings coincide to a greater or lesser extent.

In order to facilitate their handling, the hollow bodies of the various removable attachments comprise flutes 51 over a portion of their length.

FIG. 6 shows a flexible extension pipe 52 facilitating the insertion of certain of the sprays described above. One of the ends of this extension is constituted by a fixing ferrule 17 provided with its locking stud 18, whilst its second end comprises a cylindrical housing 53 formed in a manner similar to the housing 12 provided at the forward part of the body 1 of the apparatus, for the reception of the fixing ferrule 17 of the removable attachments. In this housing ferrule there is likewise formed an annular recess 54 intended to receive the stud 18 of the fixing ferrule 17 of the attachments, and into which opens a longitudinal recess 55 for engagement and disengagement of the said stud.

A joint 56 is installed in the base of the housings 12 and 53 in order to ensure fluid tightness between the surfaces in contact of the said housings and of the fixing ferrules 17 of the various removable attachment or of the extender.

It will be understood that, by simple rotation of the head 1b with respect to the handle 1a, it is possible to place the inlet conduit 7 in communication, either with the conduit 8 permitting to feed the water up to the spray head 11, or with the conduit 9 by means of which the water can be directed towards the removable attachment installed in front of the said head.

FIGS. 11 to 25 illustrate another manner of construction of the hydraulic apparatus for bodily hygiene according to the invention and which, in this case, is equipped with a pulsator permitting to obtain, when desired, an outflow of pulsated water or a continuous outflow.

The parts of this apparatus which are identical or which carry out a function analogous to that of the apparatus precedingly described are designated by the same references.

According to this manner of construction, a means is provided to immobilise the rotary part or head 1b of the body 1 in the desired position, and such a means could likewise be provided for the simplified apparatus already described. This means is, for example, constituted by a ball 57 urged by a spring 58 housed in a recess formed in one of the parts (for example part 1b) of the body 1, the other part (part 1a) of which comprises a circular trough in the base of which are provided small cavities for the positioning of the said ball.

Three channels 59,60 and 61 are formed in the rear portion of the rotary part or head 1b of the body, these channels terminating in a wide transversal cavity 62 of the said head.

In the upper part of this cavity there is housed a hydraulic pulsator below which is installed a second selector.

The selector 63 (FIGS. 13 and 14) is installed in the lower part of the cavity 62 with a capability of rotating. It has a trunco-conical form and comprises a base 63a provided with holes 64 spaced at 90 degrees and from which rises a circular lateral wall 63b. In this wall there are formed two cylindrical inlet openings 65 and 66 and an outlet opening 67. The openings 66 and 67 are diametrically opposed, whilst the opening 65 disposed between the two former ones is spaced at 45 degrees with respect to the opening 66.

One or the other of the openings 65 and 66 is placed in communication with the channel 61, in the two positions of the selector 63, whilst the opening 67 can be placed, or not, according to the position of the selector, in communication with a channel 74 formed in the head 1b and communicating with the coupling mouth piece 12, preferably by means of the cavity 13.

The selector 63 is coupled to the body 1, with a capability of rotation, by means of a ring 68 fixed on the said body, for example by means of screw 101, and placed in contact against a peripheral shoulder 63c on the said selector. An annular fluid tight joint 69 is placed at the point of meeting of the body 1, the rotary selector 63 and the fixed ring 68.

Laterally, and below the shoulder 63c, the selector has a circular recess 70 of an amplitude of 45 degrees, in which is housed a lug 71 integral with the fixed ring 68, the opposed ends of the said recess determining the two functional positions of the said selector.

A spray head 72 provided with perforations 73 is fixed at the lower part of the selector 63, for example by threading or pinning. In this manner, the spray head 72 is integral in rotation with the selector 63, for which it constitutes an operating member.

The pulsator designated in its entirety by the reference 75 in FIG. 13 comprises a fixed housing having a lower part 76 and an upper part 77, for example assembled by screwing.

The lower part 76 (FIGS. 16 and 17) is constituted by a cup of cylindrical shape comprising a base 76a and a lateral wall 76b extending up from said base and bounding, with this latter, a chamber 78. In the base 76a are formed four holes 79 spaced at 90 degrees for the passage of the water in the direction of the spray head 72, through the holes 64 of the selector 63, when the position of this latter permits this flow. The wall 76b is provided with an entry opening 80a and an outlet opening 80b, diametrically opposed and capable of being placed, or not, in communication with the channel 61 and with the channel 74, through the cylindrical openings 65 or 66 and 67, respectively, of the selector 63, according to the position of this latter.

The derivation cup 76 is housed at the interior of the selector 63 on the base 63a of which it rests and its openings 79 communicate, or not, with the openings 64 of the said base, according to the position of the said selector. Annular joints 81 are disposed about the inlet of the holes 64, in order to ensure fluid tightness between the base 76a of the derivation cup 76 and the base 63a of the selector 63, when this latter is placed in the position preventing the passage of water in the direction of the spray head.

In the upper part of the derivation cup 76 there is fixedly installed, for example by means of threading, a disc 82 rigidly fast with a central pivot 83 orientated upwardly (FIGS. 18 and 19).

Four holes 84,85 are formed in the disc 82, with a spacing of 90 degrees for the passage of the pulsated water. One of these holes (hole 84) has a supplementary recess for the passage of the operating water.

A turbine 86 (FIGS. 20 to 22) is housed in the upper member 77 of the housing of the pulsator. This turbine is supported by the pivot 83 and it is likewise guided in rotation by an upper pivot 87 axially on the upper wall 77a of the upper member 77 of the housing.

At its upper part, the turbine 86 is provided with blades 88 spaced regularly about all of its periphery. The lower part of this turbine is hollowed, and the lateral wall 86b of this hollowed part 100 comprises an opening 89 of an amplitude of 180 degrees. The lateral wall 86b is furthermore provided with vertical external flutes 90 and internal flutes 91.

The upper member 77 of the housing of the pulsator comprises an upper wall 77a and a cylindrical lateral wall 77b extending towards the base from the upper wall. It is provided, at its upper part, with a demi-circular lateral trough 92. This trough communicates with the internal hollowing of the member 77, by means of a plurality of passages 93 constituting as many ejectors permitting the formation of fine jets of water assuring the rotation of the turbine 86 housed in the said member. The trough 92 is placed in permanent communication with the channel 59.

In its lowest part, the element 77 is provided with an opening 94 establishing a permanent communication between the channel 60 and the interior of the said member.

A longitudinal recess 95 is formed in the internal surfaces of the lateral wall 77b, for the evacuation of the water assuring the rotation of the turbine 86, in the direction of the derivation cup 76.

At its upper part, the member 77 is provided with a stud 96 cooperating with a recess 97 formed in the cavity 62 of the head 1b, in order to assure the positioning and the immobilisation in rotation of the housing of the pulsator, in order that the holes and openings of the said housing shall be perfectly positioned with respect to the various channels, openings and holes with which they are or can be placed in communication.

A stopper 98 screwing into a thread of the upper inlet of the cavity 62 permits the immobilisation in translation of the housing 76–77 of the pulsator. A fluid tight joint 99 is disposed between the surfaces in contact of the stopper 98 and of the cavity 62.

The apparatus thus formed comprises:
an inlet conduit 7;
a first distribution conduit terminating at the spray head 72 and constituted by the passages 61-65-80a-64-10 (spray with continuous output), or by the passages 60-94-89-100-84 and 85-78-79-64-10 (spray with pulsated output);
a second distribution conduit terminating at the coupling mouth piece 12 and constituted by the passages 61-66-80a-78-80b-67-74-13 (feed of the attachments with continuous flow), or by the passages 60-94-89-100-84 and 85-78-80b-67-74-13 (feed of the attachments with pulsated outflow).

It will be understood that the obtaining of the continuous jets of water is obtained by placing the inlet conduit 7 in communication with the channel 61, by means of the first selector constituted by the rotary coupling of the head 1b with respect to the handle 1a and by the formation of the two members.

The water coming from the channel 61 can be directed, by means of the rotary second selector 63, either towards the spray head 72, or in the direction of the removable attachment engaged in the coupling mouth piece 12.

In the first case, the selector 63 is placed in the position in which:

its inlet opening 65 communicates with the channel 61 and with the inlet hole 80a of the derivation cup 76;

its openings 64 communicate with the holes 79 of the said derivation cup;

there is no communication between the outlet opening 80b of this latter and the channel 74 terminating at the coupling mouth piece 12.

In this second case, the selector is placed in the position in which:

its inlet opening 66 communicates with the channel 61 and with the inlet opening 80a of the derivation cup 76;

its outlet opening 67 communicates with the outlet opening 80b of the said derivation cup and with the channel 74;

there is no communication between its holes 64 and the holes 79 of the derivation cup.

In order to obtain jets of pulsated water, the conduit 7 is placed in communication with the channels 59 and 60 terminating at the pulsator 75 (FIG. 11).

The operating water coming from the channel 59 is distributed, through the recess 92, to the ejectors 93 which give rise to jets causing the rotation of the turbine 86; this water being evacuated, by means of the recess 95 and of the hole 84, to the chamber 78 of the derivation cup 76.

The water coming from the channel 60 enters into the housing of the pulsator, through the opening 94 which is alternately closed and opened, during the rotation of the turbine, according to whether it is placed opposite to the lateral wall 86b of the said turbine, or the opening 89 of this latter.

There is obtained in this manner a pulsated outflow of the water which arrives in the chamber 78 of the derivation cup 76, after having traversed the lower hollowed out portion 100 of the turbine 86 and the holes 84 and 85 of the disc 82.

Starting from the chamber 78, the pulsated water can be directed, by means of the rotary selector 63, either towards the spray head 72, or towards the removable attachment installed in the coupling mouth piece 12, in the manner indicated above.

The frequency of the pulsations can be lowered by diminishing the outflow of water in the conduit 59 by partial closing off of this conduit at its junction with the conduit 7 of the body 1a; the spaced positions of the ball 57 in its circular recess permit the more or less exact coincidence between the conduits 7 or 59.

In another manner of construction of the hydraulic apparatus for bodily hygiene according to the invention, the pulsator device is disposed between the mixer tap and the spray flexible pipe.

Figure 27:
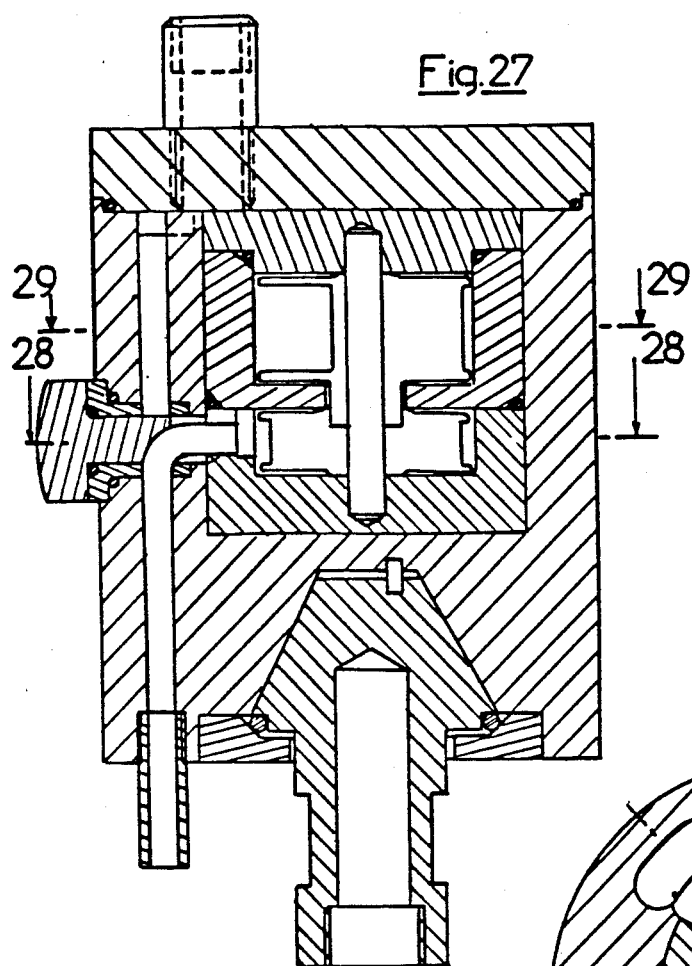
FIG. 27 is a view in axial section of a pulsator adapted to be disposed between a mixer tap and a flexible douche hose.
Figure 28:
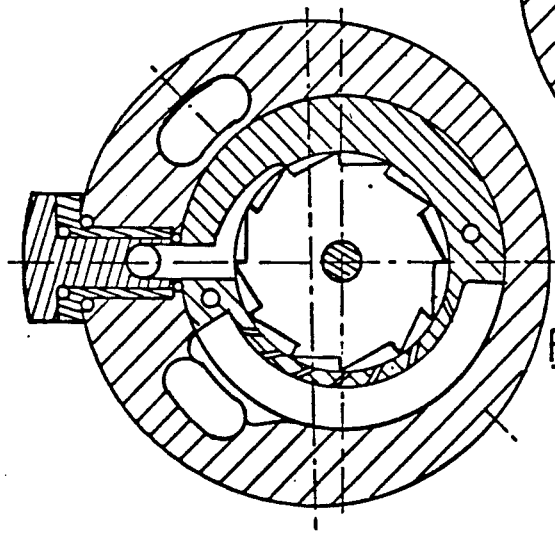
FIG. 28 is a section on the line 28—28 of FIG. 27.
Figure 29:
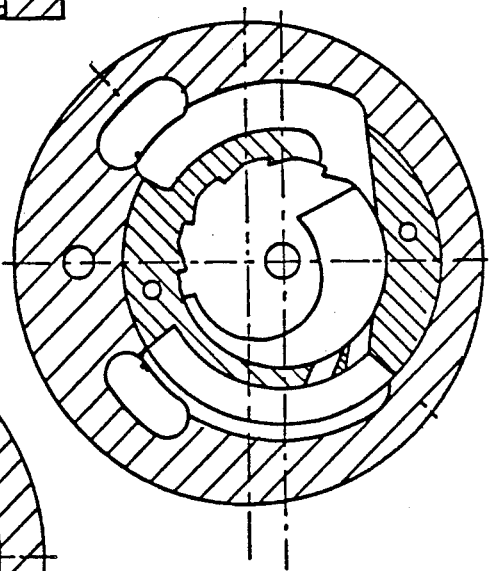
FIG. 29 is a section on the line 29—29 of FIG. 27.

FIG. 27 shows an axial section of this device, and two sections at the position of the turbine respectively, in its moving and pulsating parts.

In this manner of construction, the water having served for driving of the turbine can, by means of a rotary button, be returned again to the exterior of the apparatus (increase of intensity of the pulsations) or mixed with the outflow of pulsed water (diminution of the intensity of the pulsations).

What we claim is:

1. Hydraulic apparatus for bodily hygiene comprising a body of which a portion is arranged as a head and another portion is arranged to constitute a handle provided with threading permitting its coupling to a flexible pipe, the body being provided internally with at least two distribution conduits together with a two-position selector and an inlet conduit enabling the inlet conduit to be placed in communication with either one of said distribution conduits according to the position of said two-position selector; one of the said distribution conduits opening into a wide cavity arranged in the head portion of the apparatus, the wide cavity being bounded on at least one side by a spray head; the second of the said distribution conduits communicating with a coupling mouthpiece disposed in the said head portion; the apparatus also including a removable hydaulic bodily hygiene treatment attachment provided with a fixing ferrule for coupling to the said mouth piece.

2. Apparatus according to claim 1, wherein a cavity for soluble substances and provided with a fluid tight closing means is arranged in the body portion of the apparatus, said cavity being disposed upstream of the coupling mouth piece and communicating both with the said mouth piece and with said second distribution conduit.

3. Apparatus according to claim 2 wherein a strainer is installed in said cavity for soluble substances.

4. Apparatus according to claim 1 wherein the handle portion and the head portion of the body are joined one as an extension of the other by means of mutually engaging plane end surfaces, a coupling device being provided about said mutually engaging plane end surfaces such as to enable assembly of the two portions in fluid type manner, whereby permitting rotation of the said head, this arrangement constituting said two-position selector.

5. Apparatus according to claim 1 wherein the coupling mouth piece and the fixing ferrule of the removable attachment are provided with complementary assembling means permitting securement of the said attachment with freedom of rotation.

6. Apparatus according to claim 1 wherein the removable attachment is constituted by a buccal spray comprising a flattened forward portion forming a rectangular surface provided with rows, transversely spaced, of perforations, these perforations being formed at the crossing points of mutually transverse straight lines.

7. The apparatus according to claim 1 wherein the removable attachment is constituted by a buccal spray, said buccal spray comprising a flattened forward portion forming a rectangular surface provided with rows of spaced transversal openings.

8. Apparatus according to claim 1, wherein an output limiter is interiorly mounted in association with the fixing ferrule for said removable attachment.

* * * * *